(12) United States Patent
Clawson (10) Patent No.: US 7,592,181 B2
(45) Date of Patent: Sep. 22, 2009

(54) OCCULT BLOOD TESTING DEVICE

(75) Inventor: Burrell E. Clawson, Newport Beach, CA (US)

(73) Assignee: Diagnostica, Inc., Newport Beach, CA (US)

( * ) Notice: Subject to any disclaimer, the term of this patent is extended or adjusted under 35 U.S.C. 154(b) by 290 days.

(21) Appl. No.: 11/527,059

(22) Filed: Sep. 25, 2006

(65) Prior Publication Data

US 2008/0131971 A1 Jun. 5, 2008

(51) Int. Cl.
*G01N 33/72* (2006.01)
*G01N 33/48* (2006.01)

(52) U.S. Cl. .......................... 436/66; 436/63; 436/164; 436/165; 436/169; 422/55; 422/56; 422/58; 422/61; 422/68.1; 435/287.1; 435/287.6; 435/287.7

(58) Field of Classification Search ................... 436/63, 436/66, 164, 165, 169; 422/55, 56, 58, 61, 422/68.1, 102; 435/287.1, 287.6, 287.7, 435/4

See application file for complete search history.

(56) References Cited

U.S. PATENT DOCUMENTS

| | | | |
|---|---|---|---|
| 4,071,317 A | 1/1978 | Lam | |
| 4,333,734 A | 6/1982 | Fleisher | |
| 4,365,970 A | 12/1982 | Lawrence et al. | |
| 4,382,064 A | 5/1983 | Detweiler et al. | |
| D281,903 S | 12/1985 | Duffy | |
| 4,562,043 A | 12/1985 | Mennen et al. | |
| 4,582,685 A | 4/1986 | Guadagno et al. | |
| 4,615,982 A | 10/1986 | Lawrence | |
| 4,645,743 A | 2/1987 | Baker et al. | |
| 4,738,823 A | 4/1988 | Engelmann | |
| 4,789,629 A | 12/1988 | Baker et al. | |
| 4,818,702 A | 4/1989 | Lawrence | |
| 4,937,197 A | 6/1990 | Lawrence | |
| 4,939,097 A | 7/1990 | Lawrence | |
| 4,983,416 A | 1/1991 | Hunsinger et al. | |
| 5,100,619 A | 3/1992 | Baker et al. | |
| 5,106,582 A | 4/1992 | Baker et al. | |
| 5,137,808 A | 8/1992 | Ullman et al. | |
| 5,171,529 A | 12/1992 | Schreiber | |
| 5,182,191 A | 1/1993 | Fan et al. | |
| 5,196,167 A | 3/1993 | Guadagno et al. | |
| 5,198,365 A | 3/1993 | Grow et al. | |

(Continued)

FOREIGN PATENT DOCUMENTS

WO   WO 00/8137   2/2000

OTHER PUBLICATIONS

U.S. Appl. No. 10/139,473, filed May 3, 2002.

*Primary Examiner*—Maureen M Wallenhorst
(74) *Attorney, Agent, or Firm*—Stout, Uxa, Buyan & Mullins; Frank J. Uxa (57) ABSTRACT

A self-contained system for testing for the presence of occult blood in a specimen has been provided. The system includes a housing holding a test element and a container for releasing a developing medium onto the test element. The housing includes a base portion encasing both the container and the test element, and a cover. The system further includes specimen openings and results openings having different configurations, one from the other, which provides enhanced visualization of test results. The system also includes structure, such as channels, effective to control a rate of flow of developing medium to the specimen openings.

19 Claims, 4 Drawing Sheets

U.S. PATENT DOCUMENTS

| | | |
|---|---|---|
| 5,217,874 A | 6/1993 | Guadagno et al. |
| 5,264,181 A | 11/1993 | Schreiber |
| 5,310,680 A | 5/1994 | Baker et al. |
| 5,344,762 A | 9/1994 | Karapetian |
| 5,391,498 A | 2/1995 | Baker et al. |
| 5,504,013 A | 4/1996 | Senior |
| 5,593,851 A | 1/1997 | Jackson |
| 5,668,011 A | 9/1997 | Jackson |
| 5,747,351 A | 5/1998 | Hemmati |
| 5,840,584 A | 11/1998 | Waldenburg et al. |
| 5,948,687 A * | 9/1999 | Cleator .................. 436/66 |
| 6,077,711 A | 6/2000 | Singer |
| 6,372,513 B1 | 4/2002 | Nguyen et al. |
| 6,436,714 B1 | 8/2002 | Clawson et al. |
| 6,464,939 B1 | 10/2002 | Bachand et al. |
| 7,189,356 B1 * | 3/2007 | Clawson .................. 422/56 |
| 7,195,878 B2 * | 3/2007 | Cleator .................... 435/6 |
| 7,288,413 B2 * | 10/2007 | Goulden .................. 436/66 |
| 7,427,505 B2 * | 9/2008 | LaStella .................. 436/66 |
| 2007/0092401 A1 * | 4/2007 | Liao et al. ............... 422/58 |
| 2007/0116593 A1 * | 5/2007 | Clawson .................. 422/56 |
| 2007/0259366 A1 * | 11/2007 | Lawrence et al. ......... 435/6 |

* cited by examiner

OCCULT BLOOD TESTING DEVICE

BACKGROUND OF THE INVENTION

The present invention is directed to systems and methods useful in testing for a presence of an anomalous substance in a biological specimen. More particularly, the invention is directed to a diagnostic testing system for detecting a presence of occult blood in a fecal sample, the system being suitable for at-home use by an untrained individual, as well as other areas where good results are needed and a laboratory is not readily available or timely.

Over 140,000 new persons per year in the United States are afflicted with cancer of the colon and rectum, the disease occurring equally in both men and women. Contrary to many other forms of cancer, early diagnosis and treatment of colorectal cancer and its precursor polyps does result in a cure rate of 80% to 90%. If, however, the disease is not detected until the later stages, the cure rate drops significantly. Thus, early detection of the disease is important to successful treatment of colorectal cancer. For this reason, it is recommended that all individuals over age 50 with no family history of the disease be screened annually for colorectal cancers. Individuals with family history of the disease or other known risk factors should be screened annually beginning no later than age 40.

Conventional screening procedures consist of testing for occult (hidden) blood in stool samples provided by a patient. Typically, the patient must collect two separate specimens on a test card on each of three consecutive days, and then deliver the test cards to a laboratory. At the laboratory, a physician or lab technician rehydrates the samples and then applies developer liquid to each specimen's test element, which has previously been impregnated with a suitable chromogenic reagent, such as guaiac. If blood is present in the specimen, the chromogenic reagent will cause the test element to change colors when the developer fluid is added, indicating that fecal occult blood or a similar reactant has been found.

One factor deterring individuals from undergoing their recommended annual screening is the natural revulsion which many, if not most, people feel toward handling and looking at fecal matter. This revulsion may be amplified by the lack of a suitable implement for obtaining a specimen and applying it to the test element. Most test kits simply provide a wooden coffee-stirrer type stick which is somewhat difficult to manipulate and often, because of its generally smooth exterior surface, does not pick up a large enough sample or retain the sample without risk of dropping some of the fecal matter. Another unpleasant factor is the inconvenience and, sometimes, embarrassment associated with transporting or mailing the fecal matter specimens to a testing laboratory in a paper envelope.

In order to eliminate or reduce the aforementioned problems, various attempts have been made to develop a convenient test kit which requires a minimum of handling of fecal specimens, and can be performed by an untrained individual in the privacy of his or her own home. Examples of such attempts are disclosed in U.S. Pat. Nos. 4,582,685 and 5,196,167 to Guadagno et al., and U.S. Pat. No. 5,840,584 to Waldenburg. None of these prior art test kits have successfully met all of the needs of in-home users, however, and none has been approved by the United States Food and Drug Administration for over-the-counter sale.

An especially advantageous test kit is disclosed in Clawson et al., U.S. Pat. No. 6,436,714, having common inventorship herewith. Another advantageous test kit is disclosed in U.S. patent application Ser. No. 10/139,473, filed on May 3, 2002, now U.S. Pat. No. 7,189,356, issued on Mar. 13, 2007, and having common inventorship herewith.

The disclosure of each of the patents, patent publications and other publications identified herein is incorporated herein in its entirety by this specific reference.

There is still a need for improved test kits that are easy to use, hygienic and are effective in detecting even faint traces of a substance, such as fecal occult blood, in a biological specimen.

SUMMARY OF THE INVENTION

Systems for testing for the presence of a substance in a biological specimen are provided. The systems are relatively inexpensive and simple to manufacture and are designed to be especially easy to use by an ordinary individual. The systems provide a user-friendly tool for detecting faint, but sometimes significant, traces of a substance, such as an anomalous substance, for example, occult blood, in a biological specimen, for example, a fecal specimen.

The present systems generally comprise a test element, for example, a lateral flow test strip, having a medium entrance portion and a results portion, a container holding a developing medium and structured to release developing medium to the medium entrance portion, and a housing holding the test element and the container. The housing includes at least one specimen opening and at least one results opening. A portion of the test element is exposed at each of the specimen and results openings. The system preferably further comprises an applicator element for facilitating hygienic, effective application of a biological specimen to the system, for example, to the specimen opening.

Generally, the specimen opening is located and structured to expose a portion of a first side of the test element which receives a biological specimen to be tested. For example, the specimen opening is structured to receive a biological specimen, for example, a small amount of a fecal specimen, onto the portion of the test element that is exposed by the specimen opening. The results opening is located and structured to expose a portion of an opposing, second side of the test element where visual test results can be observed. Generally, the specimen opening and the results opening are located to expose substantially directly opposing portions of the test element.

Advantageously, in one aspect of the invention, the specimen opening and the results opening have different configurations, one from the other. Advantageously, the different configurations are effective to provide enhanced, for example, improved and/or more easily readable and/or more useful to the user of the system and/or more definitive and/or more distinctive and/or the like, visualization of test results relative to an identical system having a specimen opening and a results opening having identical configurations. This feature is very important in that the system user is able to better visualize the results of the test so that he/she has more confidence in the accuracy of the test results when searching for the lowest levels of hidden blood. Moreover, the system, including this feature is more user friendly and reliable and, ultimately provides benefits not present in the prior art.

For example, the specimen opening may be defined by a first area and the results opening may be defined by a second area that is larger than the first configuration.

In some embodiments, the specimen opening has a first length and the results opening has a second length that is greater than the first length. Additionally or alternatively, the specimen opening may have a first width and the results opening may have a second width that is greater than the first width. In other embodiments, the specimen opening has a first width and the results opening has a second width substantially equal to the first width such that the results opening is longer but not necessarily wider than the specimen opening. Various other configuration distinctions are possible and are considered to be within the scope of the invention.

In another aspect of the invention, the system further comprises a flow control structure effective to control, for example, increase, a rate of flow of developing medium from the container to the medium entrance portion of the test element, relative to an identical system not including the flow control structure.

In some embodiments, the flow control structure is configured to provide a non-uniform distance between the housing and the test element over a area extending from the container to the medium entrance portion.

For example, the flow control structure comprises a channel or a plurality of channels defined in the housing and generally extending between the container and the medium entrance portion. The channels may be structured to increase a rate of flow of developing medium to the results portion of the test element relative an identical system having no channels. For example, the channels may have a depth, width and/or configuration effective to control a rate of flow of the developing medium to the medium entrance portion.

Alternatively or additionally, the flow control structure may comprise a roughness, porosity, texturing, thickness, or other characteristic of a portion of the test element, for example, a portion of the test element extending between the container and the medium entrance portion, the characteristic effective to control, for example, increase, a flow of the developing medium relative to an identical system having a test element without the characteristic.

The present systems, including the flow control structure, provide substantial benefits. For example, the flow control structure is often effective to direct the flow of developing medium to the medium entrance portion of the test element thus ensuring that an appropriate or adequate amount of the developing medium will interact with the specimen, thereby facilitating obtaining an accurate test result. In addition, when, as is very useful, the rate of flow of the developing medium is increased relative to a system without the flow control structure, the developing medium interacts with the specimen more quickly and an accurate test result is obtained in a shorter period of time. Further, the flow control structure is useful for providing an enhanced accuracy correctness or reliability of the test results relative to an identical system without the flow control structure. In short, the flow control feature of the present invention allows for increased control of the present system and its use, with the resulting benefits of more effectively facilitating obtaining reliable accurate test results, often in a shorter period of time, which benefits can be highly advantageous to the user of the present systems.

In other embodiments of the invention, the housing comprises a plurality of specimen openings and a plurality of results openings generally aligned with the plurality of specimen openings. The flow control structure may comprise a plurality of channels extending between the container and the medium entrance portion.

In other more specific aspects of the invention, the housing may be made up of a base portion encasing both the container and the test element and a moveable cover for selectively covering and uncovering the base. The housing may include cambered regions or other structures for securing the test element in place in the housing in order to limit movement or sliding of the test element, especially during application of a specimen onto the test element. The cover may be further provided with a tab which can be manipulated with a finger of one hand, and the base is provided with tabs which can be grasped easily with one or two other fingers of the same hand, thus allowing the cover to be easily opened and closed with only one hand.

In embodiments in which an applicator is provided, the applicator preferably comprises a handle portion configured to be grasped by a user and a distal portion for collecting a specimen to be applied to the test element. The handle portion and the distal portion may be removably attached to the housing prior to use thereof. The applicator is preferably configured to facilitate hygienic handling of a biological specimen such as a fecal specimen. In some embodiments, the distal portion of the applicator is configured for optimal retrieval and uniform spreading of the specimen into the specimen opening. In some embodiments, the applicator comprises two identical applicator portions which are joined together to form an extended applicator for facilitating handling of a specimen. The housing and removably attached applicator may be molded from thermoplastic polymeric material.

Instructions for use may be printed on the various components of the system. These instructions preferably indicate both the order in which the steps of the testing procedure are to be performed, and the location for carrying out the steps. Thus, steps to be performed with the cover closed are provided on the cover, steps to be performed with the cover open are provided on the top portion of the base, and steps to be performed with the housing inverted (and the cover closed) are provided on the bottom portion of the base. This reduces the chance of any confusion on the part of the user, and increases the likelihood that the test will be performed correctly and accurate results obtained.

Each and every feature and combination of two or more features described herein is included within the scope of the present invention provided that the features included in the combination are not mutually inconsistent.

These and other aspects and advantages of the present invention may be more clearly understood and appreciated with reference to the following detailed description, when considered in conjunction with the accompanying drawings in which like parts bear like reference numerals.

DETAILED DESCRIPTION OF THE DRAWINGS

Figure 1:
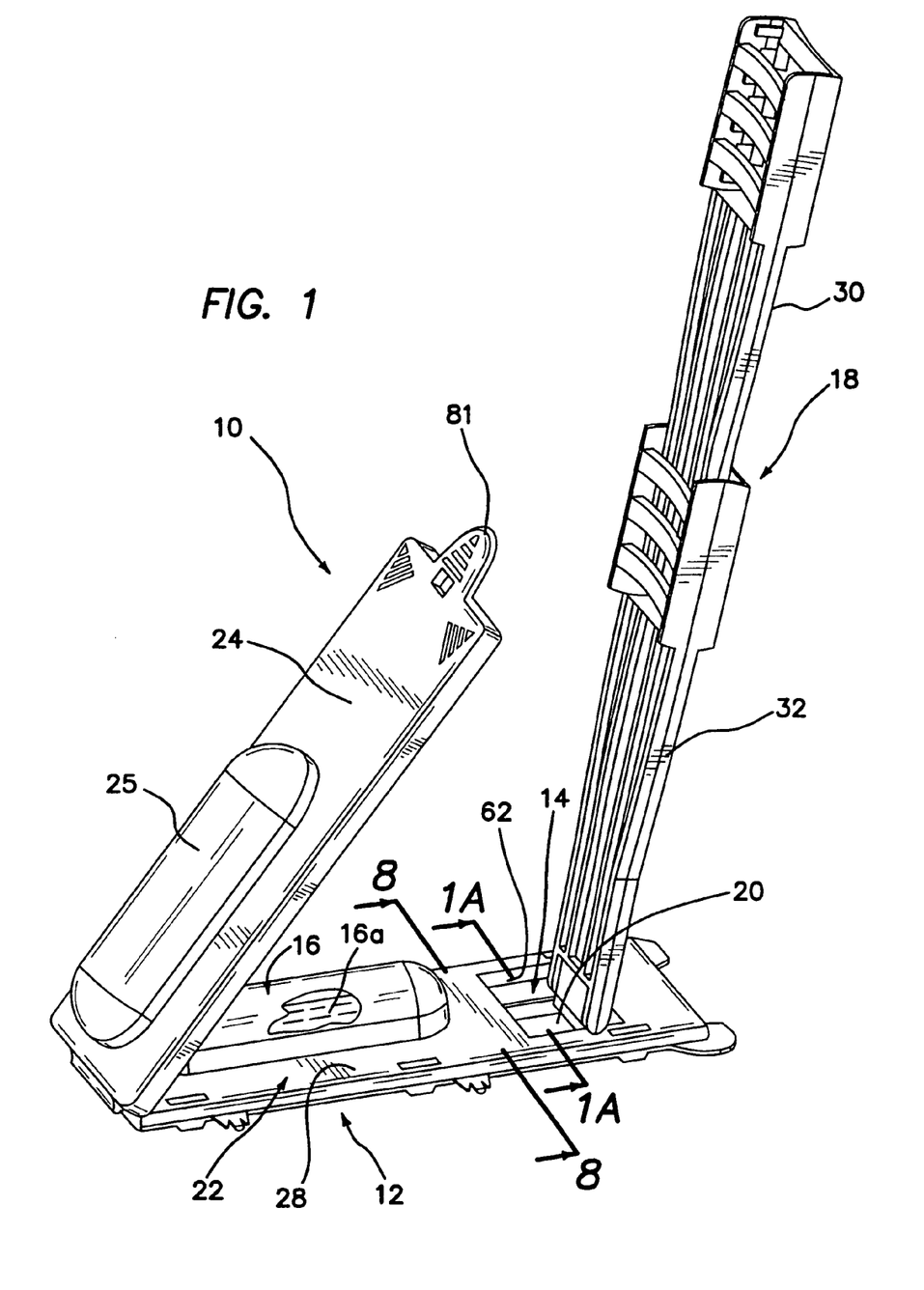
FIG. 1 is a perspective view of a system for testing for fecal occult blood in accordance with the present invention, with a portion broken away to show interior detail.
Figures 1A, 3, 4, 8:
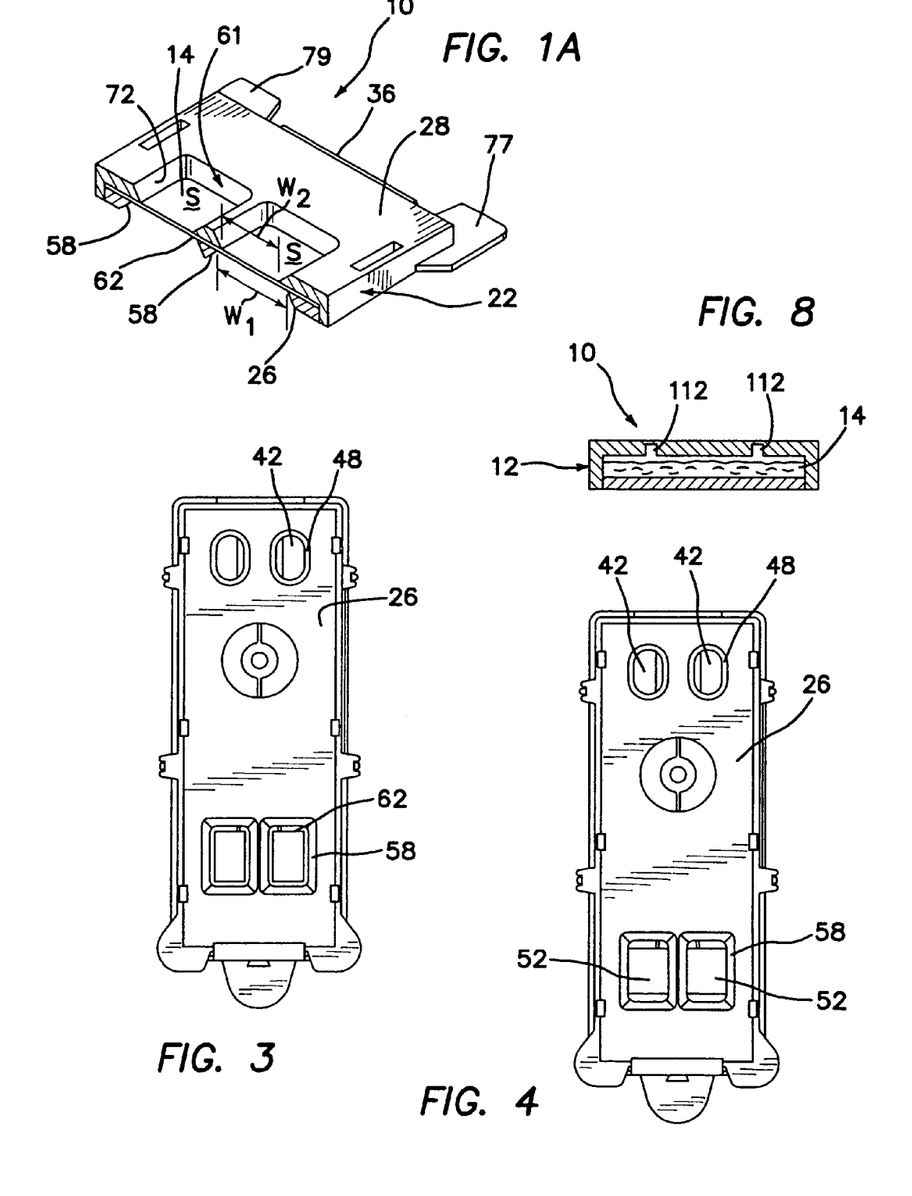
FIG. 1A is a cross sectional view of the system shown, taken along lines 1A-1A of FIG. 1.
FIG. 3 is a plan view of a results viewing side of the assembled system shown in FIG. 1 with applicator removed.
FIG. 4 is a plan view of an alternative results viewing side of the assembled system shown in FIG. 1 with applicator removed.
FIG. 8 is a cross-sectional view of the system taken across lines 8-8 of FIG. 1.

FIGS. 1 and 1A show an exemplary system 10, in accordance with the invention, for testing for presence of a substance, for example, but not limited to, occult blood, in a biological specimen. The system 10 comprises a housing 12 holding a test element 14, for example, a guaiac-treated paper, and a container 16 holding a developing medium, for example, a liquid hydrogen peroxide/ethyl alcohol solution. An applicator 18 may be provided for facilitating collection of a specimen, for example, a fecal material, and application of the specimen to a specimen placement area 20 located on one side, for example, an upper side, of the test element 14.

Figure 2:
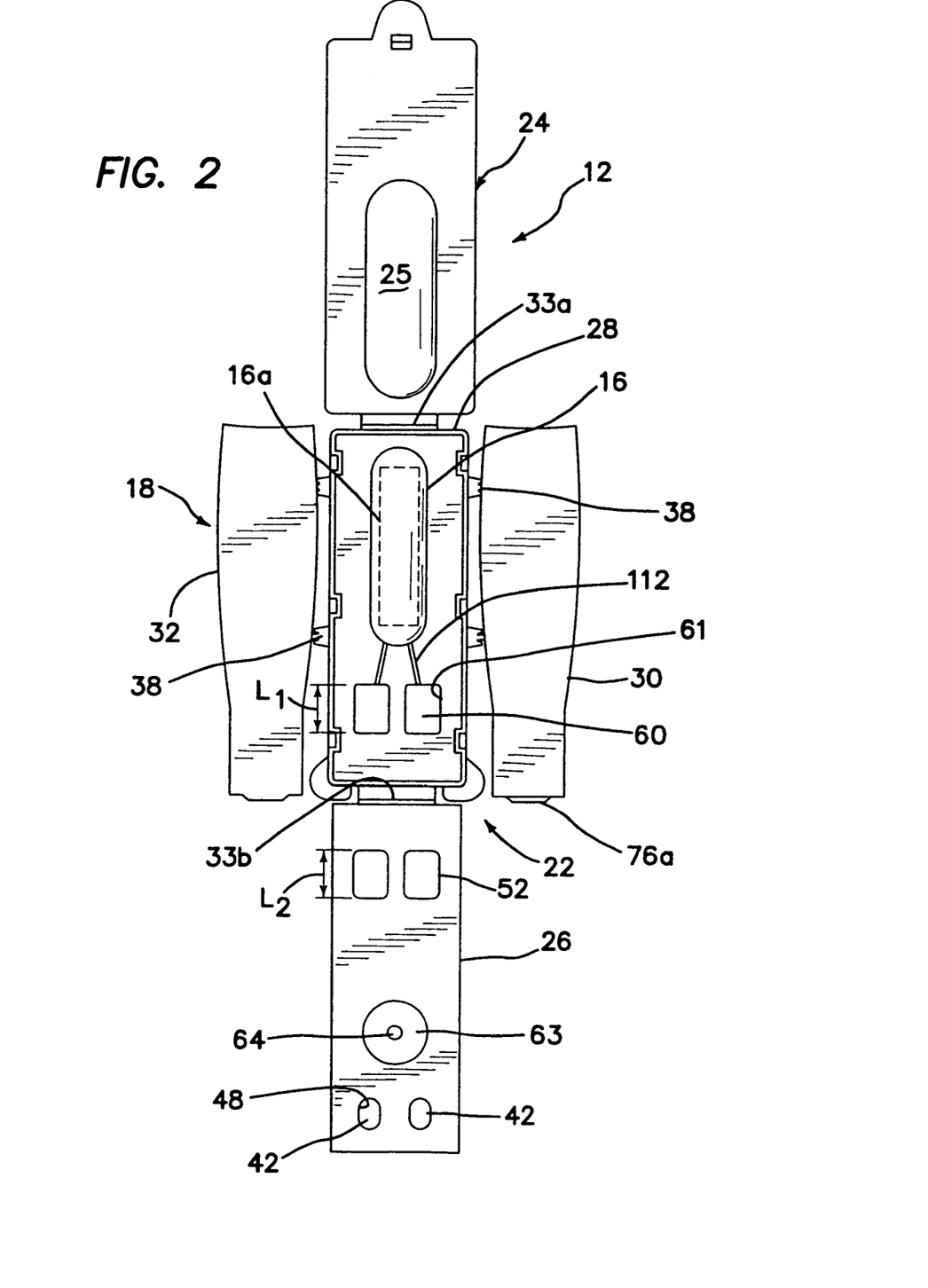
FIG. 2 is a plan view of the housing of the system in an unfolded condition prior to assembly.

Referring now to FIG. 2, the housing 12 is shown in an unassembled or unfolded configuration in order to illustrate certain features of the invention. In the shown embodiment, the housing 12 includes a base portion 22 and a cover portion 24. The cover portion 24 includes a dome-shaped protrusion 25. The base portion 22 may be made up of a bottom section 26 and a mating top section 28 between which is located a container 16 in the form of a depression, which holds an ampoule 16a (shown in dashed lines) containing a suitable amount of the developing medium. Turning briefly back to FIG. 1, container 16 appears as a protrusion on the top section 28 of the base portion 22, in the view shown. Ampoule 16a is shown within the container 16 at the cut-away region.

Turning back to FIG. 2, applicator portions 30 and 32, which are structured to fit together to form applicator 18 shown in FIG. 1, may be integrally molded with the housing 12.

In a preferred embodiment of the invention, the housing 12 and applicator portions 30 and 32 are made from a unitary or single piece of molded plastic or polymeric material. The cover 24 is flexibly joined to the base portion 22 at hinged region 33a and the bottom section 26 is flexibly joined to the top section 28 at hinged region 33b.

The applicator portions 30, 32 may be frangibly coupled to the housing 12 by elements 38. Other embodiments of the invention may provide the applicator portions 30, 32 separately from the housing 12, for example, and/or in a single piece, as a pair of non-identical pieces or more than two pieces. Similarly, it should be appreciated that the various portions of the housing may be made of separate elements that are individually molded rather than being molded together as a single foldable piece as shown.

When the system 10 is assembled for use, the housing 12 is folded about hinged regions 33a and 33b to form the configuration shown in FIG. 1. The test element 14 is secured between the bottom section 26 and the top section 28 of the base portion 22.

FIG. 1 shows the system 10 being used to test for the presence of occult blood in a fecal specimen. Ampoule 16a may comprise a breakable sealed glass cylinder. The ampoule 16a is located in the container 16 and is contained between bottom section 26 and mating top section 28 which form the base portion 22 of the housing 12. More specifically, the test element 14 and ampoule 16a have been placed underneath the top section 28 of the base 22 and the bottom section 26 of the base 22 has been folded up against the top section 28, locking the test element 14 and ampoule 16a into position. The cover 24 can be latched over the specimen placement openings to prevent contamination of the test element 14 during transport.

Referring now to FIG. 2 with additional reference to FIG. 3, in the embodiment shown, the bottom section 26 of the base portion 22 has two validation openings, for example, generally oblong-shaped validations openings 42, which serve as windows for enabling viewing validation areas of the test element 14. The validation openings 42 may include beveled edges 48, shown most clearly in FIG. 3 and FIG. 4, for enhancing viewing of the validation areas.

As further shown, the bottom section 26 includes results openings 52 which may be substantially rectangular in form. As shown most clearly in FIG. 3, the results openings 52 may include beveled edges 58.

As shown in FIG. 2, the top section 28 of the base portion 22 is provided with two specimen openings 60. The specimen openings 60 are configured and located to receive a specimen to be tested, for example a spreadable specimen, for example, a fecal specimen, when the housing is assembled for use. Turning now as well to FIGS. 1 and 1A, when the system is assembled for use, specimen openings 60 having edges 61 and results openings having by edges 58, expose, respectively, substantially opposing portions of the test element 14.

In the embodiment shown, the specimen openings 60 and the results openings 52 have different configurations, one from the other. This differing of the configurations provides enhanced visualization of test results relative to a system having specimen openings and results openings having identical configurations.

As shown in FIGS. 1A and 3, results opening 52 is sized and shaped to expose an extended portion 62 of the test element 14. Thus, in FIG. 1A, it can be seen that in this embodiment, width $W_1$ of results opening is greater than width $W_2$ of specimen opening. The differing configurations of the specimen opening 60 and the results opening 52, which form the extended portion 62 on the results side of the test element 14, provides a region, or regions, of enhanced visualization of test results relative to a system having a specimen opening and a results opening of identical configurations.

As shown in FIG. 2, the specimen opening 60 is defined by a first area and the results opening 52 is defined by a second area that is larger than the first area.

For example, the specimen opening 60 has a first length $L_1$ and the results opening 52 has a second length $L_2$ that is greater than the first length $L_1$. Further, the specimen opening 60 may have a first width and the results opening may have a second width that is greater than the first width.

The differing configurations between the specimen opening 60 where a specimen is applied, and the results area, where results are viewed, provide enhanced visualization of test results, especially when the specimen tested contains only a very faint trace of the substance, such as occult blood, being detected, for example, in a fecal specimen. The present system 10 has been found to provide higher accuracy, particularly in the detection of very low levels of occult blood, relative to system in which a results opening and a specimen opening are identically configured.

Thus, it will be appreciated that the present system 10 is advantageous in detecting very early signs of disease in certain instances, thereby enabling a user to seek medical treatment, or at least further diagnostic testing, at a possible early stage of a disease.

Although not wishing to be bound by any particular theory of operation, it is believed that when a fecal specimen is applied to the specimen area through opening 60, and the developer fluid is released onto the test element 14, the fluid components of occult blood in the specimen tend to bleed outward from the specimen area and are separated from the solid components of the specimen. Even trace amounts of these blood components are detectable on the extended region 62 (see FIGS. 1A and 3) of the results side of the test element. For example, a fine blue line may appear in extended region 62 where no blue is visible elsewhere through the results opening 52.

Turning back now to FIGS. 1 and 2, a circular depression 63 is located adjacent the validation openings 42 and the results openings 52. A protuberance 64 is located in the center of the depression 63. The depression 63 and protuberance 64 enables a user to compress and break the ampoule 16a when the protuberance 64 is pressed against a hard, flat surface such as a table or counter top.

Additional detail regarding assembly of the applicator 18 from applicator portions 30 and 32, application of a specimen to the specimen opening using applicator 18, breaking of the ampoule to release developing medium and other information that may be useful for gaining a better understanding of the invention may be found in U.S. patent application Ser. No. 10/139,473, and U.S. Pat. No. 6,436,714, both which have been incorporated by reference in their entireties herein.

Figures 5, 6, 7:
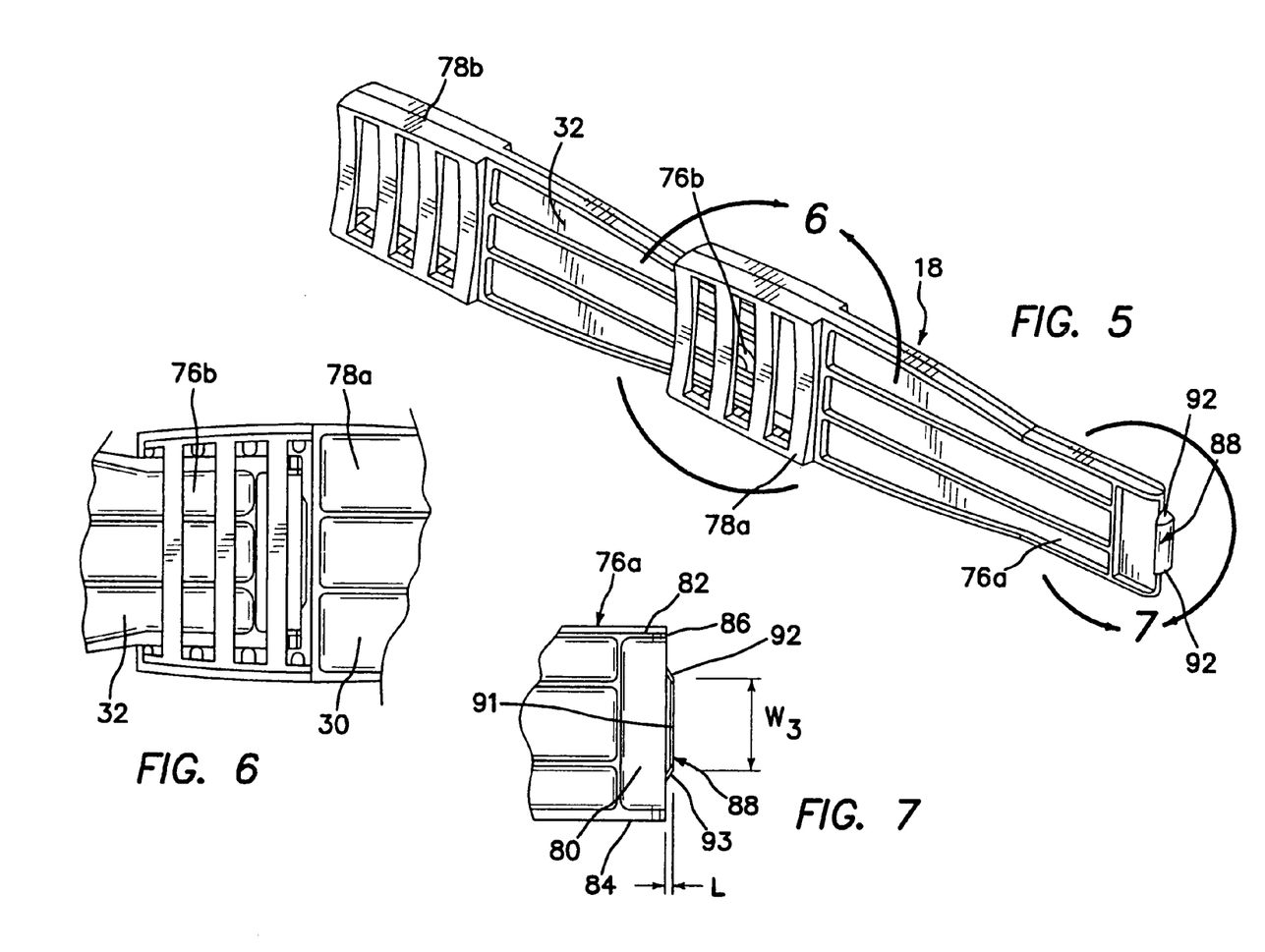
FIG. 5 is a perspective view of an applicator assembly in accordance with the present invention.
FIG. 6 is an enlarged plan view of the encircled area 6-6 of FIG. 5.
FIG. 7 is a plan view of the encircled area 7-7 of FIG. 5.

Turning now to FIG. 5, when applicator portions 30, 32 are assembled as shown to form applicator 18, portion 32 may serve as a handle to be grasped by the user, while the distal end 76a of the distally positioned portion 30 serves as a specimen collector and spreader.

Referring now to FIG. 7, in the embodiment shown, the spreader or distal end 76a of the applicator 18 includes a generally planar front surface 80, a generally planar rear surface (not shown) and a pair of side walls 82, 84. The front and rear surfaces are recessed with respect to the side walls 82, 84 and form a shoulder 86. A spreading tip 88 extends distally of the shoulder 86.

The features of the spreading tip 88 may be better appreciated after considering the design of the specimen openings 60, as shown in detail in FIGS. 1 and 2. Specifically, the specimen openings 60 are defined by beveled, inwardly sloping generally trapezoidal walls 72. The inwardly sloping walls assist in positioning a specimen onto a specimen placement area S of the test element 14 which is revealed through the openings 60. The walls 72 and the specimen placement area S define a recess with enough volume to receive and hold a suitable amount of a fecal sample to be tested.

Referring as well to FIG. 5, the spreading tip 88 of applicator 18 is defined between opposing edges 92, 93 which may have a cone angle conforming to the beveled side walls 72 of the specimen openings 60. In a preferred embodiment of the invention, the width $W_3$ of the spreading tip 88 is substantially equal to or slightly larger than the width $W_2$ of the specimen openings 60. Generally, the distal tip 88 and adjacent shoulders 86 are configured to substantially correspond to the shape of the specimen opening 60 to enable mating engagement of the applicator opposing edges 92 and 93 with the walls 72 of the opening 60. When mated together, the distal tip 88 and specimen placement zone S define a gap or clearance in which the specimen is received. In other words, the structure results in a constant clearance between the distal tip 88 of the applicator 18 and the test element 14, allowing the user to easily apply the specimen in a layer of fairly uniform thickness, regardless of moderate changes of the angle of which the applicator 18 is held relative to the specimen opening 60.

The distal spreading tip 88 may include textured or otherwise enhanced surfaces in order to increase an amount of specimen material collected by the applicator 18 and minimize the likelihood of the specimen material falling off. For example, the distal tip 88 may have a textured surface comprising a multitude of small bumps yielding a sandpaper-like finish. Other surface features, such as grooves, fins, dimples or the like, that increase the effective surface area and holding power of the tip can also be used. Alternatively, the retentiveness of the surface could be enhanced with coatings having adhesive properties or an affinity for the specimen to be tested.

Turning back now to FIG. 2 with additional reference to FIG. 8, system 10 may further comprise flow control structure effective to control a rate of flow of the developing medium from the container 16 to the medium entrance portion of the test element 14. For example, the flow control structure may comprise a non uniform distance between the test element and the housing. For example, the flow control structure may comprise a channel 112 or a plurality of channels defined in the housing 12. In the shown system 10, two channels 112 are provided, each extending between the container 16 and one of the specimen openings 60. When the ampoule 16a in the container 16 is broken to release the developing medium to the test element, for example, when the test is being performed by a user as described elsewhere herein, at least a portion of the medium will be directed, or channeled, toward the specimen openings 60. The channels 112 enable the medium to flow at a faster rate toward the specimen relative to an identical system having no flow control structure. When the system is structured for use in testing for the presence of occult blood in a fecal specimen, it has been found that the channels 112 assist the developing medium in reaching the specimen in a more "real time" period, relative to an identical system not including channels.

The channels 112 may be structured, for example, have a desired depth or width, to achieve a desired flow rate. Further, rather than a singular flow channel located between the container and a specimen opening, the structure for controlling rate of flow may comprise multiple grooves/ridges disposed in a desired alignment between the container 16 and the specimen opening. For example, the grooves/ridges may be aligned generally in a fan shape directed from the container and diverging outwardly toward the specimen openings 60.

Other structures effective to control the medium flow rate are also contemplated. For example, in the event that it is advantageous that a developing medium to pass to a specimen at a relatively slow rate, for example, over a relatively long time period, the structure for controlling flow rate may comprise barriers or restrictions, for example, folds defined in the test element, such folds being oriented substantially perpendicular to the direction of flow.

Alternatively or additionally, the flow control structure may comprise a roughness, porosity, texturing, thickness or other characteristic of the test element at a portion of the test element extending between the container 16 and the medium entrance portion of the test element 14. For example, by providing a test element 14 having a textured surface, the flow of the medium can be effectively retarded or slowed relative to an identical test element having a relatively smoother surface.

While this invention has been described with respect to various specific examples and embodiments, it is to be understood that the invention is not limited thereto and that it can be variously practiced within the scope of the following claims. For instance, the ease of use features disclosed can successfully be used with fecal blood testing kits employing polyclonal or monoclonal antibody systems, or any other alternatives to the guaiac-based chemistry system disclosed in International Patent Application No. PCT/US99/17594. The features may also be used in both chemical and non-chemical systems for revealing the presence of a wider variety of anomalous substances other than blood, such as parasites, for instance, in feces or other spreadable specimens.

What is claimed is:

1. A system for testing for the presence of a substance in a biological specimen, comprising:
   a test element having a medium entrance portion and a results portion;

a container holding a developing medium and structured to release the developing medium to the medium entrance portion; and a housing holding the test element and the container, the housing including a specimen opening and a results opening, the test element being located in the housing so that a portion of the test element is exposed by each of the specimen and results openings, the specimen opening and the results opening located to expose directly opposing portions of the test element, and having different configurations, one from the other, so that the specimen opening is defined by a first area and the results opening is defined by a second area larger than the first area, the different configurations being effective to provide enhanced visualization of test results relative to an identical system having a specimen opening and a results opening having identical configurations.

2. The system of claim 1 wherein the specimen opening has a first length and the results opening has a second length greater than the first length.

3. The system of claim 1 wherein the specimen opening has a first width and the results opening has a second width greater than the first width.

4. The system of claim 1 wherein the specimen opening has a first width and the results opening has a second width substantially equal to the first width.

5. The system of claim 1 wherein the specimen opening has a first length and a first width and the results opening has a second length greater than the first length and a second width greater than the first width.

6. The system of claim 1 wherein the test element comprises a lateral flow test strip.

7. The system of claim 1 further comprising a flow control structure located in the housing or the test element and effective in increasing or slowing a rate of flow of the developing medium from the container to the specimen opening.

8. The system of claim 1 wherein the housing comprises a flow control structure effective in increasing a rate of flow of the developing medium from the container to the specimen opening.

9. The system of claim 8 wherein the flow control structure comprises a channel extending between the container and the specimen opening.

10. The system of claim 9 which includes a plurality of the channels.

11. The system of claim 1 which is effective to detect the presence of occult blood in a fecal specimen.

12. A system for testing for the presence of a substance in a specimen, the system comprising:

a test element having a results portion and a medium entrance portion;

a container holding a developing medium and structured to release the developing medium to the medium entrance portion;

a housing holding the test element and the container and including a specimen opening and a results opening, the test element being located in the housing between the specimen opening and the results opening, the specimen opening and the results opening located to expose directly opposing portions of the test element; and a flow control structure located in the housing or the test element and effective in increasing or slowing a rate of flow of the developing medium from the container to the specimen opening.

13. The system of claim 12 wherein the flow control structure is located in the housing and is configured to provide a non-uniform distance between the housing and the test element over an area between the container and the specimen opening.

14. The system of claim 12 wherein the flow control structure is effective in increasing or slowing a rate of flow of the developing medium to the specimen opening relative to an identical system without the flow control structure.

15. The system of claim 12 wherein the flow control structure comprises a channel in the housing and is effective in increasing a rate of flow of the developing medium from the container to the specimen opening relative to an identical system without the flow control structure.

16. The system of claim 15 wherein the flow control structure comprises a plurality of channels in the housing.

17. The system of claim 12 wherein the housing comprises a plurality of the specimen openings and a plurality of the results openings, each one of the specimen openings and a different one of the results openings being located relative to each other to expose directly opposing portions of the test element.

18. The system of claim 17 wherein the flow control structure comprises a plurality of channels in the housing and is effective in increasing a rate of flow of the developing medium from the container to the specimen openings relative to an identical system without the flow control structure.

19. The system of claim 12 wherein the specimen opening and the results opening have different configurations, one from the other, so that the specimen opening is defined by a first area and the results opening is defined by a second area larger than the first area, the different configurations being effective to provide enhanced visualization of test results relative to an identical system having a specimen opening and a results opening having identical configurations.

* * * * *